Figure 1:
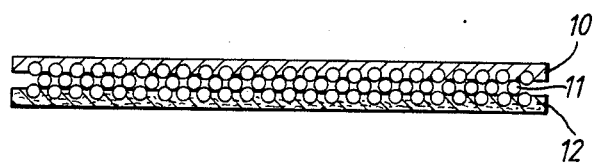

United States Patent [19]

Banks et al.

[11] Patent Number: 4,921,702
[45] Date of Patent: May 1, 1990

[54] SHEET MATERIAL FOR TREATING WOUNDS IN PLANT MATTER

[75] Inventors: Nigel H. Banks, Palmerston North, New Zealand; Colin A. Borton, Gros-Islet; Francis S. Leonce, Castries, both of West Indies; Terence J. Lomax, Manchester; Antony R. H. Meier, Hertfordshire; Christopher J. Skiba, Lincolnshire, all of England.

[73] Assignees: Haircloth Weaving & Finishing Company Limited, Lancashire; Geest Industries Limited, Lincolnshire; The Windward Islands Banana Growers Association, St. Lucia, all of England.

[21] Appl. No.: 184,291

[22] Filed: Apr. 21, 1988

[30] Foreign Application Priority Data

Apr. 24, 1987 [GB] United Kingdom ................ 8709802

[51] Int. Cl.$^5$ ........................................... A01N 25/34
[52] U.S. Cl. .......................................... 424/404; 47/8; 424/411; 424/443; 424/445; 428/240; 428/283; 428/284; 428/252; 428/246; 428/289; 428/325; 428/327; 428/907; 428/913
[58] Field of Search ............... 428/283, 284, 252, 246, 428/289, 913, 325, 327, 907, 240; 47/8; 424/404, 443, 445, 411, 413

[56] References Cited

U.S. PATENT DOCUMENTS

| | | | |
|---|---|---|---|
| 1,999,458 | 4/1935 | Hollister | 424/413 |
| 4,766,695 | 8/1988 | Harlow | 424/411 |

FOREIGN PATENT DOCUMENTS

| | | |
|---|---|---|
| 348755 | 5/1931 | United Kingdom . |
| 456554 | 11/1936 | United Kingdom . |
| 570428 | 7/1945 | United Kingdom . |
| 806762 | 12/1958 | United Kingdom . |
| 906911 | 9/1962 | United Kingdom . |
| 1384537 | 2/1975 | United Kingdom . |
| 2074437 | 11/1981 | United Kingdom . |

Primary Examiner—James J. Bell
Attorney, Agent, or Firm—Marshall, O'Toole, Gerstein, Murray & Bicknell

[57] ABSTRACT

An absorbent sheet material for application to plant wounds comprises a flexible laminate of sheet material (the distal layer) and a permeable layer (the proximal layer), the layers being bonded together and the laminate containing in the proximal layer or between the layers, liquid absorbing solid particles and/or fibrous absorbent material and the laminate containing or having its proximal surface coated with a biologically active material which is a biostat or a biocide.

17 Claims, 1 Drawing Sheet

SHEET MATERIAL FOR TREATING WOUNDS IN PLANT MATTER

The present invention is concerned with treating wounds in plant matter (such as fruit or vegetables) and with a sheet material for use in such treatment.

When certain fruit and vegetables are harvested it is necessary to cut them from the plant. For example, when bananas are harvested, a hand is cut from the plant leaving a wound on the hand at the crown and a corresponding wound on the plant. These wounds tend to exude sap or latex which, in the case of crown wounds, may flow over the crown and the individual bananas and when dry, spoil their appearance, in some cases to such an extent as to make them unsaleable. Such wounds, both on the crown and on the plant, also serve as a point of attack for pathogenic organisms, such as those which cause crown rot decay of bananas (such as *Fusarium pallidoroseum* and *Colletotrichum musae*).

Similar problems arise on harvesting many other fruits and vegetables, such as pineapples, mangoes, papayas, asparagus, cucumbers and lettuce, and also when cutting a living tree or bush as, for example, when pruning, trimming or shaping, or when tapping a rubber tree for latex, or any other tree for sap.

The conventional method of treating such wounds in bananas is by washing complete hands or clusters (parts of a hand) in running water to remove latex therefrom, followed by applying to the wound (for example, by spraying or dipping) a solution of a fungicide of low mammalian toxicity, such as thiabendazole or benomyl. A disadvantage of this method is that it involves handling the fruit in several stages which can lead to the fruit being damaged or bruised. Further, if carried out on a commercial scale, it requires a substantial capital investment in washing plant, treatment vats, etc. and is therefore generally unsuited to banana-growing areas where the individual plantations are relatively small. Further this method presupposes banana plantations in which the terrain is such that harvested bananas can be rapidly transported to a central treatment station; in some banana-growing areas, the terrain effectively rules this out.

One technique used in such washing stations is to dip the crowns of the banana hands or clusters into a solution of aluminium sulphate or alum (which acts as a coagulant for latex bleeding from the wounds) before washing. However, this method does not staunch the flow of latex early enough so that thorough washing of the hands must still be carried out.

In our British Patent 2074437 we have described a different approach to this problem which basically comprises applying an absorbent sheet material to the plant wound. While it is open to the grower to use such a material as he wishes, the intention is that a supply of such material should be carried by each field worker and that he should apply it to the crown and stem wounds after the hands are cut from the stems; it is recommended that such application should not be made immediately when the hand is cut from the stem, but after a short delay of, for example 2 minutes, during which the major flow of latex takes place. The sheet material described in the British patent is a porous absorbent sheet material which comprises a porous web having a dry coating on one or both surfaces, the coating comprising an intimate mixture of water-soluble adhesive polymer, a biologically active material (that is a biostat such as a fungistat and/or a bacteristat, or a biocide, such as a fungicide and/or a bactericide), and latex coagulant.

Whilst this material performs very satisfactorily under a range of field conditions, there are circumstances in which it would be desirable to have a material with greater absorbency. We have also found that if the absorbency of such a material is substantially increased, it is not necessary for such a material to include a latex coagulant.

To this end, we have developed an improved absorbent sheet material for use on plant wounds and, according to the present invention, we provide such a sheet material which comprises a flexible laminate of a sheet material (the distal layer) and a permeable layer (the proximal layer), the layers being bonded together and the laminate containing in the proximal layer or between the layers, liquid absorbing solid particles and/or fibrous absorbent material, and the laminate containing or having its proximal surface coated with a biologically active material (as herein defined).

The proximal layer forms the side (surface) of the sheet material which is applied to the plant wound; the distal layer forms the other side (surface) of the sheet material.

The liquid absorbing particles which may be used in the sheet material according to the invention may be of any of the synthetic polymeric materials which have been developed as liquid absorbents. Such materials are used in disposable nappy liners for babies and in incontinence pads.

These materals fall into two broad groups; the polyelectrolytes and the non-electrolytes, of which the former are more important due to their higher functionality. Most of these materials fall into one of four classes: polyacrylic and methacrylic acid derivatives, malic anhydride/vinyl monomers copolymers, polyacrylonitriles, and polyvinyl alcohols.

The polyacrylic and polymethacrylic acid derivatives include both homopolymers and copolymers of the acids with acrylic and methacrylic acid esters. Such polymers and copolymers are usually polymerised to form a water soluble polymer which is then rendered insoluble by cross-linking. The polymer may be cross-linked with a multivalent cation, by radiation, or with a cross-linking agent. The cross-linked polymer or copolymer may also be saponified to form free carboxyl groups; the number of ionizable groups, usually carboxylates, and the cross-linking density, determine the absorbency of the product.

The cross-linking density not only affects the absorbency, but also the time it takes to absorb and the strength of the gel formed. Generally, the higher the cross-linking density, the faster the uptake of liquid and the stronger the gel formed.

For the purpose of the present invention, it is generally preferred to use cross-linked polyacrylic acid derivatives, such as cross-linked sodium polyacrylate, as the particulate absorbent. Suitable commercially available materials which are understood to be of this kind are Salsorb 86 (trade mark; available from Allied Colloids) and Favor SAB (trade mark; available from Stockhausen).

The particle size of the absorbent particles is not critical and a wide range of particle sizes can be used. It is generally preferred that the particle size should be from 100 to 600 $\mu$m.

Since the efficiency of some of the particulate absorbents referred to above is pH dependent, a buffering agent may be incorporated with the particulate absorbent to ensure that absorption takes place at the optimum pH.

Instead of or in addition to the liquid absorbing solid particles, the sheet material of the invention may comprise fibrous absorbent material, such as cellulose fluff. A particular advantage of such fibrous materials is that they absorb liquids substantially instantaneously, while certain of the solid particulate absorbents referred to above exhibit a short delay between coming into contact with a liquid and the onset of absorption. A sheet material of the invention in which a fibrous absorbent material, such as cellulose fluff, is the sole absorbent or one of the absorbents, will generally be thicker and more cushioned than an otherwise similar material containing only a particulate absorbent and the former type of sheet material will provide a further advantage, that is it will provide mechanical cushioning of the crowns which without any covering or cushioning can bruise or otherwise damage other hands or clusters of bananas when a number of hands or clusters are packed for shipment in the same carton or other container.

A further, optional liquid absorbent which may be used in the material of the invention is clay.

The sap or latex exuded by the wound may cause staining of the fruit, particularly in the case of bananas, if it is not removed or prevented from reaching the surface of the fruit. To reduce the staining of the fruit by any sap or latex which is not absorbed by the sheet material of the invention, the latter may further contain any suitable anti-staining additive; aluminium sulphate can be used for this purpose.

The proximal layer of the sheet material of the invention must be permeable (so that the sap or latex can pass through it) and it is preferably absorbent. The proximal layer may be and preferably is a preformed permeable or perforated sheet material, such as a lightweight, for example 30 g/m$^2$, cellulose tissue or a permeable or perforated woven or nonwoven synthetic polymeric sheet material. Alternatively, it may be a layer of cellulose fluff or similar loose fibrous material. In the latter case, an adhesive and, if desired, a particulate absorbent and the biologically active material, is/are mixed with the fluff so that the proximal layer has sufficient coherence to withstand the conditions of field use.

The primary function of the distal layer is to provide the necessary mechanical strength to the laminate, that is so that the laminate can be handled under field conditions without disintegrating and further, preferably, so that when the sap or latex flow from the wound has been staunched and the exuded sap or latex has dried, the laminate can be removed cleanly from the wound. It will usually be considered undesirable to sell fruit produce, such as banana hands, with a plant wound dressing such as herein described and it is therefore desirable that the dressing material should be strong enough to be removed, as by peeling off, from the plant material.

At the same time, the distal layer should not be stiff or board-like as this would make it difficult or impossible to apply the laminate to the plant wounds under field conditions.

The distal layer may be an impermeable or only slightly permeable flexible membrane so that sap or latex is physically prevented from passing through the sheet material of the invention. In this type of embodiment, the distal layer may be formed of any suitable polymeric sheet material, such as polyethylene. Alternatively the distal layer may have some liquid absorbing capacity so as to further increase the absorbency of the material. In this case, preferred materials for the distal layer include absorbent cellulosic papers, for example a cellulosic paper of 50 g/m$^2$ which is capable of absorbing 6 times its own weight of water, and absorbent woven or nonwoven synthetic polymeric sheet materials.

A laminate of such an absorbent material and an impermeable membrane as previously described may also be used as the distal layer, the impermeable membrane being positioned, preferably, on the outside.

Any suitable adhesive may be used to bond together the proximal and distal layers of the laminate. Preferred adhesives for this purpose include, for example, polyethylenes having a high melt flow index and polyamides. It is particularly preferred to form the material of the invention as individual sachets, that is units of square, rectangular, circular or other shape which are sealed round part of the whole of their peripheries with adhesive, or by heat sealing, or by mechanical means, such as crimping.

The term "biologically active material" is used herein to mean a biostat, such as a fungistat and/or a bacteristat, or a biocide, such as a fungicide and/or a bactericide. Since many of the economically important diseases of fruit or plants are due to fungal infections, it will usually be preferred to include a fungicide in the sheet materials according to the invention. The biologically active material used in the present invention should have low mammalian toxicity when the material is used for treating fruit or vegetables intended for consumption. Suitable materials include, for example, thiabendazole, benomyl, thiophanate methyl, prochloraz, and imazalil (all fungicides), dichlorophen (a fungicide and bactericide), quaternary ammonium bactericides, and mixtures of two or more thereof. It is preferred that the biologically active material used in the invention should be water-soluble or water-emulsifiable; for ease of incorporation in the material according to the invention, the biologically active material is preferably used in the form of a wettable powder. Such powders which are formulated for agricultural and horticultural use conventionally contain powdered diluents, such as clay, and dispersing agents in addition to the biologically active material.

A typical absorbent sheet material according to the invention will, for example, contain:
- 25–75, say 30, g/m$^2$ of particulate absorbent, (preferably having a particle size of 100–600 $\mu$m),
- 5–20, say 8, g/m$^2$ of high melt flow index polyethylene as adhesive, (preferably having a particle size of 250–300 $\mu$m, and
- 1.5 g/m$^2$ of fungicide as wettable powder (typically providing 0.9 g/m$^2$ of active fungicide in the case of thiabendazole wettable powder).

Figure 2:
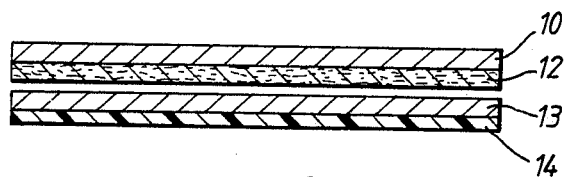
Figure 3:
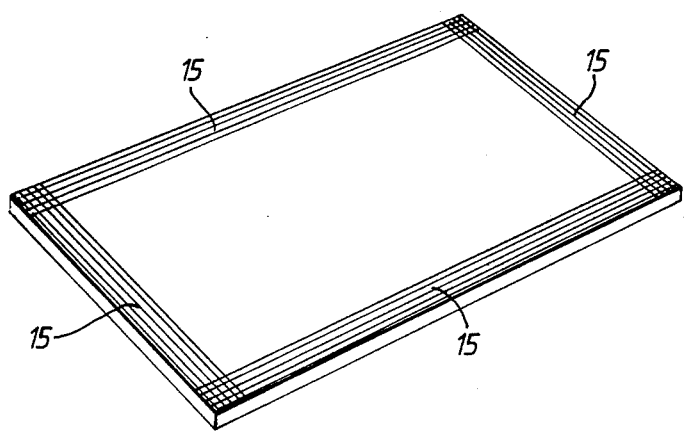

For the better understanding of the invention, preferred embodiments thereof will now be described, by way of example, with reference to the accompanying drawings, in which:

FIG. 1 is a diagrammatic section through a first embodiment of absorbent laminate with the layers shown separated in order to show the structure thereof, FIG. 2 is a diagrammatic section through a second embodiment of absorbent laminate with certain layers shown separated in order to show the structure thereof, and FIG. 3 is a diagrammatic perspective view of the embodiment of FIG. 2.

The laminate of FIG. 1 comprises a proximal layer 10 of an absorbent cellulose sheet material of 50 g/m², a layer 11 of a powder mixture of water absorbent polymeric particles as described above and powdered polyethylene having a high melt flow index, and a distal layer 12 of a lightweight non-woven synthetic polymeric sheet material. The material of layer 10 is impregnated or coated with a fungicide and a dye (to distinguish the proximal layer of the laminate).

The assembly of layers 10, 11 and 12 is bonded together over the whole area of the assembly under heat and pressure, for example, by heating the assembly in an oven to the softening temperature of the powdered polyethylene and then passing it through a pair of nip rolls. In the finished product the layer 11 is indistinguishable since the absorbent polymeric particles become pressed into the fibrous layers on either side.

The laminate of FIG. 2 comprises the laminate of FIG. 1, that is comprising layers 10, 11 and 12 as already described though layer 11 cannot be seen as already described, and a further layer 13, 14 which consists of creped Kraft paper 14 which has been pre-coated with a layer 13 of polyethylene.

The layers 10, 12 are bonded to the layer 13, 14 by heat sealing round the marginal zones 15 as shown in FIG. 3. The creped paper layer 14 of the final laminate forms the distal surface.

As compared with the laminate of FIG. 1, the laminate of FIG. 2 is better able to retain the absorbent particles because of the heat sealed marginal zones, is stronger because of the additional layer 13, 14 (and thus easier to peel off the wound when the material has to be removed), and also has better impermeability on the distal surface.

In terms of performance, the embodiment of FIGS. 2 and 3 is the better, but it is more expensive than the embodiment of FIG. 1 and in situations where the cost of the plant wound material is critical and/or the particular plants or fruits being treated do not impose a high demand on the material, the embodiment of FIG. 1 will be preferred.

The laminates of the invention can be made by building up on a continuous web of the sheet material forming the distal layer. Thus the distal layer web is advanced horizontally under a scatter coating machine which deposits a metered amount of powder blend comprising the particulate absorbent, the adhesive and any optional additives (which blend may be prepared by grinding the ingredients together or by blending previously formed powders) on to the surface of the web. The powder coated web is then passed into an oven where the assembly is heated to a temperature at which the powdered adhesive is softened, and the coated web is then passed together with a continuous web of the proximal layer (where the layer is preformed sheet material) through a pair of nip rolls to form the laminate.

When the proximal layer is not a preformed sheet material, but a material such as cellulose fluff, the material of the layer is mixed with the powder blend referred to above and the mixture is uniformly spread on to the distal layer web, and the whole is heated and pressed as described.

The proximal layer is preferably identified as such, for example, by suitable indicia or plain or patterned colouration so that the user can readily appreciate which side of the material should be applied to the wound.

The laminate may be in the form of discrete pieces of a suitable shape (square, rectangular, or other) and size, preferably bonded or sealed around their peripheries, or may be in the form of a roll or an elongated web with transverse perforations at regular intervals so that a suitable length of laminate can readily be torn from the roll.

In order that the invention may be more fully understood, the following example is given by way of illustration only:

EXAMPLE

An absorbent laminate was made by passing a continuous web of a lightweight cellulose sheet weighing 50 g/m² (forming the distal layer) under a scatter coating machine which deposited a metered amount of the following powder blend on it.

30 parts by weight of Salsorb 86 particulate absorbent having a particle size of 100–600 μm.

8 parts by weight of powdered high melt flow index polyethylene having a particle size of 250–300 μm, and 1.5 parts by weight of thiabendazole wettable powder.

The rate of application of the powder blend was such that the web was coated with 30 g/m² of the Salsorb, 8 g/m² of the powdered polyethylene, and 1.5 g/m² of the thiabendazole (corresponding to 0.9 g/m² of thiabendazole active compound). The powder coated web was then passed through an oven in which the powder was heated to a temperature sufficient to soften the polyethylene. Outside the oven, a continuous web of single layer cellulose tissue weighing 30 g/m² (forming the proximal layer) was applied to the softened powder coating and the two webs were passed through a pair of nip rolls to form a laminate.

This laminate was cut into rectangular pieces measuring 10 cm×7.5 cm and applied to the cut crowns of harvested banana hands. The effectiveness of the laminate in preventing crown rot, latex staining, and other undesirable conditions was compared with that of similar sized rectangular pieces of the coated sheet material described in the Example of British Specification 2074437B.

The banana hands were harvested in the normal way. The laminate of this invention was applied immediately to the cut crown, while the coated material of 2074437B was applied after a 2 to 5 minutes latex draining period in accordance with the preferred procedure for the material.

The treated hands were then shipped by sea from the West Indies (St. Lucia) to Britian under the normal conditions for banana shipment. The hands were assessed for crown rot, latex staining, and other conditions in Britian 16 days after harvesting. The results obtained are as follows:

|  | Laminate of invention | Material of 2074437 |
| --- | --- | --- |
| Number of hands assesed | 1810 | 1838 |
| Packing damage | 1.4% | 1.9% |
| Average weight per box | 28.2 lb | 27.9 lb |
| 1st grade | 1.4% | 0.8% |
| 2nd grade | 87.3% | 83.0% |
| 3rd grade | 9.0% | 13.3% |

-continued

|  | Laminate of invention | Material of 2074437 |
|---|---|---|
| 4th grade | 2.3% | 2.9% |
| Severe crown rot | 2.7% | 3.9% |
| Severe latex staining | 2.0% | 2.1% |
| Rust | 0% | 0% |
| Flower thrips | 0% | 0% |
| Scarring | 0.1% | 0% |

The results obtained with the two materials are generally similar, but the incidence of severe crown rot was less with the laminate of the present invention. The latter was more convenient to use in the field during harvesting as the laminate was applied to the cut crowns immediately, that is without the necessity for a latex draining period.

Claims:

1. An absorbent sheet material for application to plant wounds, which comprises a flexible laminate of a sheet material (the distal layer) and a permeable layer (the proximal layer), the layers being bonded together with the laminate containing in the proximal layer or between the layers, liquid absorbing solid particles and/or fibrous absorbent material and the laminate containing or having its proximal surface coated with a biologically active material which is a biostat or a biocide.

2. A sheet material according to claim 1, in which the liquid absorbing particles are formed of a water absorbing synthetic polymer.

3. A sheet material according to claim 2, in which the absorbing particles are formed of a crosslinked polyacrylic acid or polymethacrylic acid derivative.

4. A sheet material according to claim 1, in which the fibrous absorbent material is cellulose fluff, said fluff constituting the sole absorbent or one of the absorbents.

5. A sheet material according to claim 1, which additionally comprises clay as a liquid absorbent.

6. A sheet material according to claim 1, in which the proximal layer is a lightweight cellulose tissue or a permeable or perforated woven or non-woven synthetic polymeric sheet material.

7. A sheet material according to claim 1, in which the proximal layer consists of a layer of cellulose fluff or other loose fibrous material and contains sufficient adhesive to make the layer coherent.

8. A sheet material according to claim 1, in which the distal layer is an absorbent cellulose paper or an absorbent woven or non-woven synthetic polymeric sheet material.

9. A sheet material according to claim 8, in which the distal layer includes an impermeable or semiimpermeable coating or membrane.

10. A sheet material according to claim 1, in the form of sachets which are sealed round part or the whole of their peripheries with adhesive, or by heat sealing, or mechanical crimping.

11. A method of staunching sap or latex flow from a wound in plant matter, which comprises applying to the wound an absorbent sheet material as set forth in claim 1, the proximal surface of the sheet material being in contact with the wound.

12. A method according to claim 11, in which the absorbing particles are formed of a water absorbing synthetic polymer.

13. A method according to claim 11, in which the liquid absorbing particles are formed of a cross-linked polyacrylic acid or polymethacrylic acid derivative.

14. A method according to claim 11, in which the fibrous absorbent material is cellulose fluff, said fluff constituting the sole absorbent or one of the absorbents.

15. A method according to claim 11, in which the distal layer is an absorbent cellulose paper or an absorbent woven or non-woven synthetic polymeric sheet material.

16. A method according to claim 11, in which the distal layer includes an impermeable or semiimpermeable coating or membrane.

17. A method according to claim 11, in which the sheet material is in the form of a sachet which is sealed round at least a part of its periphery with adhesive or by heat sealing or mechanical crimping.

* * * * *